(12) United States Patent
Graeber et al.

(10) Patent No.: US 7,834,060 B2
(45) Date of Patent: *Nov. 16, 2010

(54) ADMINISTRATION OF 6-[3-(1-ADAMANTYL)-4-METHOXY-PHENYL]-2-NAPHTOIC ACID FOR THE TREATMENT OF DERMATOLOGICAL DISORDERS

(75) Inventors: Michael Graeber, Lawrenceville, NJ (US); Janusz Czernielewski, Biot (FR)

(73) Assignee: Galderma Research & Development, Biot (FR)

( * ) Notice: Subject to any disclaimer, the term of this patent is extended or adjusted under 35 U.S.C. 154(b) by 65 days.

This patent is subject to a terminal disclaimer.

(21) Appl. No.: 12/437,008

(22) Filed: May 7, 2009

(65) Prior Publication Data

US 2009/0281188 A1 Nov. 12, 2009

Related U.S. Application Data

(63) Continuation of application No. 10/937,612, filed on Sep. 10, 2004, now Pat. No. 7,579,377, which is a continuation of application No. PCT/EP03/03246, filed on Mar. 12, 2003.

(60) Provisional application No. 60/370,223, filed on Apr. 8, 2002.

(30) Foreign Application Priority Data

Mar. 12, 2002 (FR) .................. 02 03070

(51) Int. Cl.
*A01N 37/10* (2006.01)
*A01N 37/00* (2006.01)
*A61K 31/19* (2006.01)
*A61K 31/185* (2006.01)
*A61K 8/02* (2006.01)

(52) U.S. Cl. ............ 514/569; 514/577; 514/859; 424/401

(58) Field of Classification Search ............ 514/569, 514/577, 859; 424/401
See application file for complete search history.

(56) References Cited

U.S. PATENT DOCUMENTS

| | | |
|---|---|---|
| 4,717,720 A | 1/1988 | Shroot et al. |
| 5,212,303 A | 5/1993 | Shroot et al. |
| RE34,440 E | 11/1993 | Shroot et al. |
| 5,306,486 A | 4/1994 | McCook et al. |
| 5,603,940 A | 2/1997 | Candau et al. |
| 5,665,364 A | 9/1997 | McAtee et al. |
| 6,383,505 B1 | 5/2002 | Kaiser et al. |
| 6,413,536 B1 | 7/2002 | Gibson et al. |
| 7,083,799 B1 | 8/2006 | Giacomoni |
| 2003/0157138 A1 | 8/2003 | Eini et al. |
| 2005/0059740 A1 | 3/2005 | Graeber et al. |

FOREIGN PATENT DOCUMENTS

| | | |
|---|---|---|
| EP | 0 199 636 B1 | 10/1986 |
| EP | 0 487 973 A1 | 3/1996 |
| EP | 0 487 973 B1 | 3/1996 |
| FR | 2 730 930 A | 8/1996 |
| WO | WO 01/28552 | 4/2001 |
| WO | WO 02/083086 A1 | 10/2002 |

OTHER PUBLICATIONS

"Topical Formulary for Carbopol® Polymers", Noveon, Inc., The Specialty Chemicals Innovator, Pharmaceutical Polymers, pp. 1-25, Jan. 2002, Cleveland, Ohio.
Body Cream, Phytosan™, Formula No. 416.09.0077.
Jamoulle et al., "Follicular Penetration and Distribution of Topically Applied CD 271, a new Naphthoic Acid Derivative Intended for Topical Acne Treatment", *Journal of Investigative Dermatology*, (1990), 94(5), 731-732, published by Nature Publishing Group.
Allec et al., "Skin didtribution and pharmaceutical aspects of adapalene gel," *J. Am. Acad. Dermatol.* (1997) 36:S119-S125, published by American Academy of Dermatology, Inc., US.
Shroot et al., "A New Concept of Drug Delivery for Acne", *Dermatology* (1998), 196:165-170, published by S. Karger AG, Switzerland.
Rolland et al., "Site-specific Drug Delivery to Pilosebaceous Structures Using Polymeric Microspheres", *Pharmaceutical Research* (1993), vol. 10, No. 12, 1738-1744, published by Plenum Publishing Corporation.
Alirezai et al., "Etude Comparative de l'efficacité et de la tolérance de gels d'adapalène à 0,1 et 0,03 p 100 et d'un gel de trétimoïne á 0,025 p 100 dans le traitement de l'acné" (Efficacy and safety comparison study of 0.1 p. 100 and 0.03 p 100 adapalene gels and tretinoin gel in the topical treatment of acne), *Ann. Dermatol. Venereol.* (1996), 123:165-170, published by Paris Masson, Paris, France (Extensive summary in English).
Healy et al. "Acnevulgaris", *British Medical Journal*, 1994 vol. 308, Iss. 6932, pp. 2-9.
Czernielewski et al. "Adapalene biochemistry and the evolution of a new topical retinoid for treatment of acne", *Journal of European Academy of Dermatology and Venerology*, Dec. 2001, vol. 15, Supplement 3, pp. 5-12.

(Continued)

*Primary Examiner*—Sreeni Padmanabhan
*Assistant Examiner*—Samira Jean-Louis
(74) *Attorney, Agent, or Firm*—Buchanan Ingersoll & Rooney PC

(57) ABSTRACT

Dermatological disorders having an inflammatory or proliferative component are treated with pharmaceutical compositions containing on the order of 0.3% by weight of 6-[3-(1-adamantyl)-4-methoxyphenyl]-2-naphthanoic acid (adapalene) or salt thereof, formulated into pharmaceutically acceptable media therefor, advantageously topically applicable gels, creams or lotions.

35 Claims, 3 Drawing Sheets

OTHER PUBLICATIONS

Differin Gel Data Sheet (Differin Gel Data Sheet available as of Nov. 1998), pp. 1-5.

Talukdar et al., *Journal of Pharmaceutical Sciences*, May 1996, vol. 85, No. 5, pp. 537-540.

Sepicontrol A5, Aug. 2001, pp. 1-53.

International Search Report for corresponding PCT/EP03/03246 (WO 03/075908 A1) in English.

Protest Under 37 C.F.R. § 1.291 regarding U.S. Appl. No. 11/494,693 (US 2007/0043119) with attachments dated Jun. 14, 2008.

Notification of Non-entry of Protest.

European Search Report for EP 05 003144 (in English).

Minutes for Oral Proceedings for European Application EP 03712109 corresponding to parent U.S. Appl. No. 10/937,612.

Regression of total lesions

Regression of inflammatory lesions

Regression of non-inflammatory lesions

|       | 1     | 2     | 4     | 8     | 12    |
|-------|-------|-------|-------|-------|-------|
| 0.30% | -22.4 | -24.3 | -32.7 | -44.4 | -49   |
| 0.10% | -6.7  | -13.5 | -23   | -25.4 | -34   |
| Veh.  | -7.4  | -19.1 | -22.2 | -17.5 | -21.9 | week

ADMINISTRATION OF 6-[3-(1-ADAMANTYL)-4-METHOXYPHENYL]-2-NAPHTOIC ACID FOR THE TREATMENT OF DERMATOLOGICAL DISORDERS

CROSS-REFERENCE TO EARLIER APPLICATIONS

This application is a continuation of earlier U.S. patent application Ser. No. 10/937,612, filed Sep. 10, 2004, now allowed, which is a continuation of PCT/EP03/03246 filed Mar. 12, 2003, and designating the United States (published in English on Sep. 18, 2003 as WO 03/075908 A1), which claims benefit of U.S. Provisional Application No. 60/370,223, filed Apr. 8, 2002, and also claims priority under 35 U.S.C. §119 of FR-02/03070, filed Mar. 12, 2002, each earlier application being hereby expressly incorporated by reference and each assigned to the assignee hereof.

CROSS REFERENCE TO OTHER RELATED APPLICATIONS

See also copending U.S. patent application Ser. No. 12/103,182, filed Apr. 15, 2008, which is a divisional application of earlier filed co-pending U.S. patent application Ser. No. 10/937,612, filed Sep. 10, 2004, and claims the same domestic and foreign priority as claimed herein; and copending U.S. patent application Ser. No. 11/494,693, filed Jul. 28, 2006, which is a continuation-in-part of earlier filed copending U.S. patent application Ser. No. 10/937,612 filed Sep. 10, 2004, and claims the same domestic and foreign priority as claimed herein; both of said applications also expressly incorporated by reference herein and assigned to the assignee hereof.

BACKGROUND OF THE INVENTION

1. Technical Field of the Invention

The present invention relates to the administration to individuals in need of such treatment of 6-[3-(1-adamantyl)-4-methoxyphenyl]-2-naphthanoic acid, the chemical structure of which is as follows:

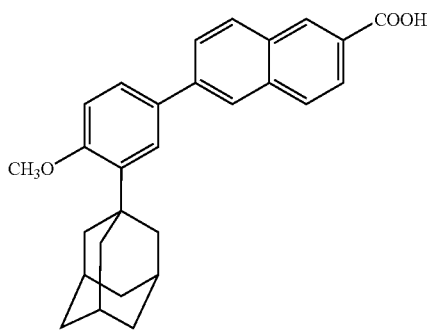

in pharmaceutical compositions, in particular dermatological compositions, for the treatment of dermatological ailments/afflictions having an inflammatory or proliferative component.

2. Description of Background and/or Related and/or Prior Art

6-[3-(1-Adamantyl)-4-methoxyphenyl]-2-naphthanoic acid (hereinafter referred to as adapalene) is a retinoid derived from naphthoic acid, having anti-inflammatory properties. This molecule has been the subject of development for the topical treatment of common acne and dermatoses sensitive to retinoids.

Adapalene is described in EP-0,199,636, and a process for synthesizing same is described in EP-0,358,574, both assigned to the assignee hereof.

The assignee hereof markets adapalene formulated at a weight concentration of 0.1% in the form of an alcoholic lotion, an aqueous gel and a cream. These compositions are suited for the treatment of acne.

Finally, adapalene is described as having a beneficial action on photodamaged skin (Photographic assessment of the effects of adapalene 0.1% and 0.3% gels and vehicle on photodamaged skin. M. Goldfarb et al., *Clinical Dermatology*, Vienna, Austria, May 2000).

SUMMARY OF THE INVENTION

Novel pharmaceutical compositions have now been developed containing adapalene at a weight concentration of 0.3% formulated into pharmaceutically acceptable media therefor, useful for the treatment (regime or regimen) of dermatological ailments, conditions or afflictions having an inflammatory or proliferative component. Specifically, it has now surprisingly been shown that, in addition to exhibiting better therapeutic efficacy compared to known compositions, the compositions according to the invention exhibits good tolerance, comparable to those of the known compositions with a lower concentration of active principle.

The results regarding tolerance observed in trials relating to photo-damaged skin (indication "photodamage"), obtained on individuals on average 65 years old, could not be exploited in the context of the present invention. Specifically, as regards use of adapalene on young individuals (in particular regarding acne with populations of teenagers or young adults), the skin exhibits very different physiopathological characteristics (presence of many lesions, in particular inflammatory lesions, modifying skin permeability, hypercornification of the follicular channel, immuno response, bacterial colonization of the skin (P. acnes), sebaceous hyperplasia with hyperseborrhea).

Figure 1:
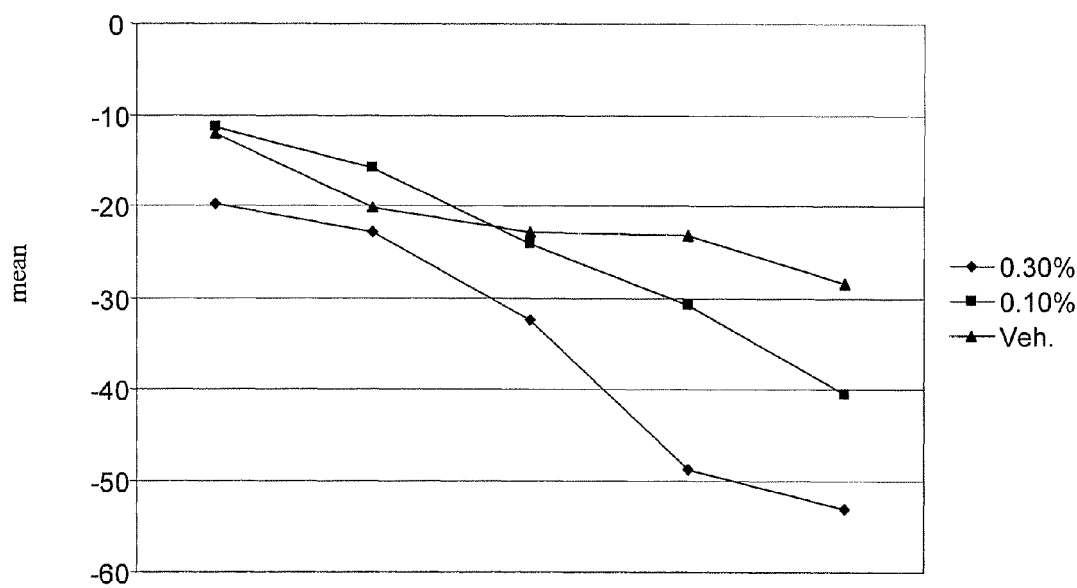
FIG. 1 is a graph illustrating regression in the number of total lesions for 0.30% adapalene gel, as compared to 0.10% adapalene gel and the gel vehicle without active ingredient, over a 12-week treatment period in groups of patients suffering from acne.

DETAILED DESCRIPTION OF BEST MODE AND SPECIFIC/PREFERRED EMBODIMENTS OF THE INVENTION

Thus, the present invention features formulating 6-[3-(1-adamantyl)-4-methoxyphenyl]-2-naphthanoic acid (adapalene), or its salts, into pharmaceutical compositions useful for the treatment of dermatological ailments, conditions or afflictions having an inflammatory or proliferative component, such pharmaceutical compositions comprising 0.3% by weight of adapalene relative to the total weight of the composition.

The term "adapalene salts" is intended to mean the salts formed with a pharmaceutically acceptable base, in particular organic bases such as sodium hydroxide, potassium hydroxide and aqueous ammonia, or organic bases such as lysine, arginine or N-methylglucamine.

The term "adapalene salts" is also intended to mean the salts formed with fatty amines such as dioctylamine and stearylamine.

The administration of the compositions according to the invention may be carried out enterally, parenterally, topically or occularly.

The pharmaceutical compositions according to the invention are preferably administered topically.

Enterally, the pharmaceutical composition may be in the form of tablets, gelatin capsules, dragées, syrups, suspensions, solutions, powders, granules, emulsions, or suspensions of microspheres or nanospheres or of lipid or polymeric vesicles for controlled release. Parenterally, the pharmaceutical composition may be in the form of solutions or suspensions for infusion or for injection.

Topically, the pharmaceutical compositions according to the invention are more particularly suited for treatment of the skin and the mucous membranes, and may be in the form of ointments, creams, milks, pomades, powders, impregnated pads, solutions, gels, sprays, lotions or suspensions. They may also be in the form of suspensions of microspheres or nanospheres or of lipid or polymeric vesicles, or of polymeric patches and hydrogels for controlled release. These compositions for topical application may be in anhydrous form, in aqueous form or in the form of an emulsion.

In a preferred embodiment of the invention, the pharmaceutical composition according to the invention is in the form of a gel, a cream or a lotion.

In particular, the pharmaceutical composition may be an aqueous gel containing in particular one or more ingredients selected from among Carbomer 940 (BF Goodrich, Carbopol 980) and propylene glycol, or a cream containing in particular one or more ingredients selected from among perhydrosqualene, cyclomethicone, PEG-20 methyl glucose sequistearate and methyl glucose sequistearate, or a polyethylene glycol-based alcoholic lotion.

The pharmaceutical compositions according to the invention may also contain inert additives or combinations of these additives, such as wetting agents;

flavor enhancers;

preservatives such as para-hydroxybenzoic acid esters;

stabilizers;

moisture regulators;

pH regulators;

osmotic pressure modifiers;

emulsifiers;

UV-A and UV-B screening agents;

and antioxidants, such as α-tocopherol, butylhydroxyanisole or butylhydroxytoluene, superoxide dismutase, ubiquinol or certain metal chelating agents.

Of course, those skilled in the art will take care to select the optional compound(s) to be added to these compositions in such a way that the advantageous properties intrinsically associated with the present invention are not, or are not substantially, adversely affected by the envisaged addition.

The formulation of adapalene into pharmaceutical compositions according to the invention is especially intended for the treatment of dermatological ailments, conditions and afflictions having an inflammatory or proliferative component, selected from the group consisting of:

common acne, comedones, polymorphous acne, nodulocystic acne, acne conglobata, secondary acne such as solar, drug-related or occupational acne;

widespread and/or severe forms of psoriasis, ichtyoses and ichtyosiform states;

Darier's disease;

actinic keratoses;

palmo plantar keratoderma and keratosis pilaris;

leucoplasias and leucoplasiform states, lichen planus;

any benign or malignant, severe and extensive dermatological preparations.

The compositions according to the invention are particularly suitable for the treatment of acne, such as common acne, and in particular for the treatment of common acne of moderate to moderately severe intensity.

Various formulations of compositions comprising 0.3% of adapalene will now be given, it being understood that same are intended only as illustrative and in nowise limitative. Also given are results showing the therapeutic effects of the compositions according to the invention and the good tolerance to same by the treated patients.

In said examples to follow, all parts and percentages are given by weight, unless otherwise indicated.

Example 1

Formulation for Topical Administration

In this example, various specific topical formulations comprising 0.3% of adapalene are illustrated.

The adapalene of the present example is provided by Sylachim, Division Finorga (product reference CF9611996).

(a) Cream:

| | |
|---|---|
| Adapalene | 3 mg |
| Carbomer 934 (BF Goodrich Carbopol 974) | 4.5 mg |
| Disodium edetate | 1 mg |
| PEG methyl glucose sesquistearate | 35 mg |
| Methyl glucose sesquistearate | 35 mg |
| Glycerol | 30 mg |
| Methyl paraben | 2 mg |
| Cyclomethicone | 130 mg |
| Perhydrosqualene | 60 mg |
| Phenoxyethanol | 5 mg |
| Propyl paraben | 1 mg |
| Sodium hydroxide quantity required for pH 6.5 +/− 0.3 | |
| Purified water | q.s. 1 g |

(b) Lotion:

| | |
|---|---|
| Adapalene | 3 mg |
| PEG 400 | 700 mg |
| Ethanol q.s. | 1 g |

(c) Aqueous Gel:

| | |
|---|---|
| Adapalene | 3 mg |
| Carbomer 940 (BF Goodrich Carbopol 980) | 11 mg |
| Disodium edetate | 1 mg |
| Methyl paraben | 2 mg |
| Poloxamer 124 | 2 mg |
| Propylene glycol | 40 mg |
| Sodium hydroxide: amount required to obtain a pH 5.0 +/− 0.3 | |
| Purified water | q.s. 1 g |

Example 2

Effectiveness of 0.3% Adapalene Gel and Comparison with the 0.1% Adapalene Gel

Tests were carried out on a population consisting of patients suffering from acne. In this population, three groups were differentiated; the first received a daily topical application of the 0.3% adapalene gel, the second a daily topical application of the 0.1% adapalene gel in the same vehicle, and the third is a control group which receives a daily topical application of the gel corresponding to the composition of the first two gels but containing no active agent.

Figure 2:
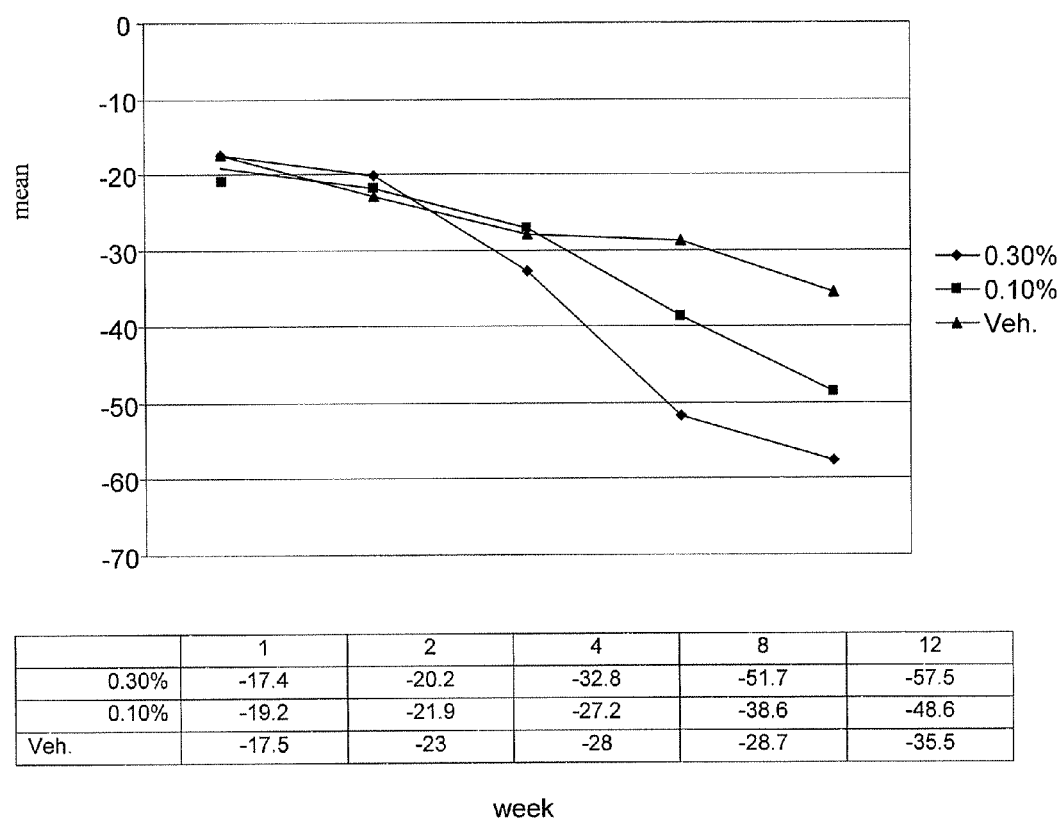
FIG. 2 is a graph illustrating regression in the number of inflammatory lesions for 0.30% adapalene gel, as compared to 0.10% adapalene gel and the gel vehicle without active ingredient, over a 12-week treatment period in groups of patients suffering from acne.
Figure 3:
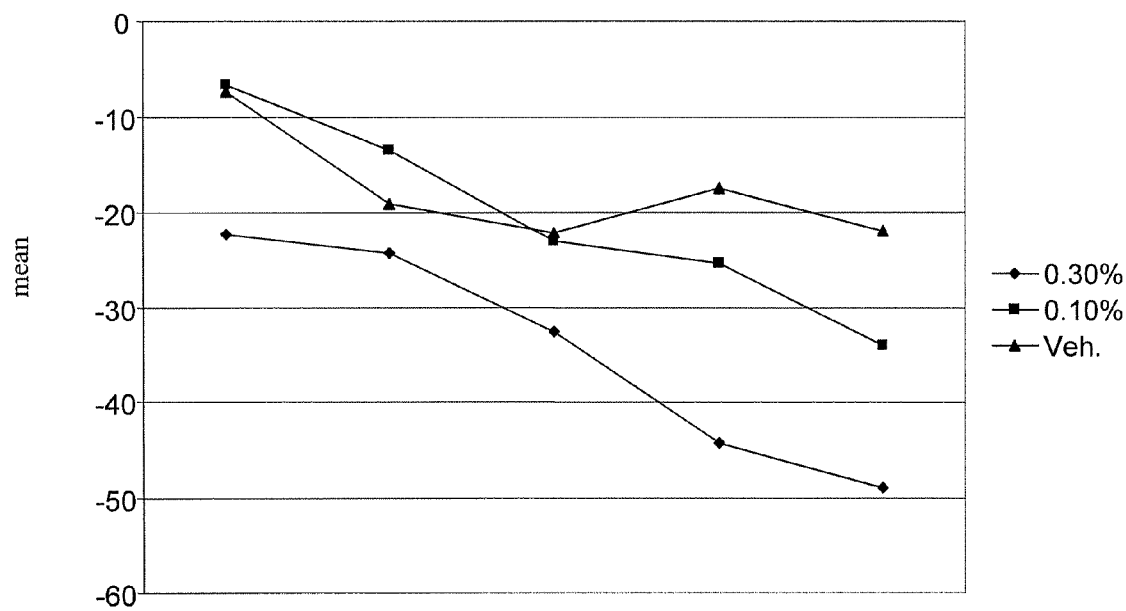
FIG. 3 is a graph illustrating regression in the number of non-inflammatory lesions for 0.30% adapalene gel, as compared to 0.10% adapalene gel and the gel vehicle without active ingredient, over a 12-week treatment period in groups of patients suffering from acne.

FIGS. 1 to 3 provide the results obtained in terms of regression of the number of lesions according to their nature.

These observations lead to the following conclusions:

the 0.3% adapalene gel acts more rapidly than the 0.1% adapalene gel; specifically, from the fourth week of treatment, a difference is noted between the effectiveness of the 0.1% adapalene gel and the 0.3% adapalene gel;

the 0.3% adapalene gel produces a clearly greater therapeutic effect after 8 weeks of treatment.

Example 3

Tolerance Regarding the 0.3% Adapalene Gel

1. Measurement of the Plasma Concentration of Adapalene:

Eight individuals suffering from common acne of medium to moderately severe intensity are treated for 10 days with 2 g of 0.3% adapalene gel applied daily over 1000 cm$^2$ of skin to be treated (face, chest and back).

Blood samples are taken on the days 1, 2, 4, 6, 8 and 10. During day 10, and following the final application, samples are taken at 1, 2, 6, 8, 10, 12, 16 and 24 hours.

The plasma concentration of total adapalene (free and conjugated) in these samples is determined using the following protocol:

enzymatic hydrolysis with a mixture of β-glucurodinase and arylsulfatase;

liquid-liquid extraction;

passage through HPLC (high performance liquid chromatography); and then fluorometric detection.

This method makes it possible to detect a minimum concentration of 0.15 ng/ml and permits quantification of the adapalene for a minimum concentration of 0.25 ng/ml.

Conclusion:

The plasma concentrations of adapalene measured after 10 days of treatment are very low and confirm the safety of daily use of the 0.3% adapalene gel.

2 a) Clinical Observation of the Side Effects Caused by Topical Administration of the 0.3% Adapalene Gel:

Two types of observation could be made:

firstly, monitoring of the patients treated within the framework of point 1 of the present Example 3 made it possible to note that tolerance to the 0.3% adapalene gel was good for all patients. They all showed signs of dryness of the skin and of desquamation with a maximum on the seventh day of treatment, these symptoms then decrease up to the end of the treatment.

2 b) Furthermore, Reference May Also be Made to the Tests Described in Example 2 Above:

In parallel to the measurements of effectiveness, the experimenters recorded the possible side effects caused, firstly, by topical application of the 0.3% adapalene gel and those caused, secondly, by application of the 0.1% adapalene gel; finally, the same observations were made on a control population to which a gel without active principle was administered.

These observations are reported in the table below.

| Local undesirable effects | 0.3% adapalene gel (N = 70) | 0.1% adapalene gel (N = 70) | Vehicle gel (N = 74) |
|---|---|---|---|
| Skin and secondary structures (nails, hair) | 31 (44.3%) | 28 (40.0%) | 5 (6.8%) |
| Dry skin | 16 (22.9%) | 13 (18.6%) | 2 (2.7%) |
| Erythema | 8 (11.4%) | 3 (4.3%) | 0 (0.0%) |
| Skin discomfort | 8 (11.4%) | 7 (10.0%) | 0 (0.0%) |
| Desquamation | 6 (8.6%) | 5 (7.1%) | 0 (0.0%) |
| Dermatitis | 3 (4.3%) | 1 (1.4%) | 0 (0.0%) |
| Pruritus | 3 (4.3%) | 1 (1.4%) | 1 (1.4%) |
| Irritant dermatitis | 2 (2.9%) | 7 (10.0%) | 0 (0.0%) |
| Local allergic reactions | 1 (1.4%) | 0 (0.0%) | 0 (0.0%) |
| Pediculosis | 1 (1.4%) | 0 (0.0%) | 0 (0.0%) |
| Contact dermatitis | 1 (1.4%) | 0 (0.0%) | 0 (0.0%) |
| Insolation | 1 (1.4%) | 3 (4.3%) | 1 (1.4%) |
| Burning sensation | 1 (1.4%) | 0 (0.0%) | 0 (0.0%) |
| Urticaria | 1 (1.4%) | 0 (0.0%) | 0 (0.0%) |
| Infection | 1 (1.4%) | 0 (0.0%) | 0 (0.0%) |
| Excoriation | 0 (0.0%) | 0 (0.0%) | 1 (1.4%) |
| Eczema | 0 (0.0%) | 0 (0.0%) | 1 (1.4%) |
| Oedema | 0 (0.0%) | 1 (1.4%) | 0 (0.0%) |

From this table, it is noted that the occurrence of undesirable side effects is statistically the same for the two gels with the different concentrations of active agent. The intensity of the undesirable side effects is average, which leads to the conclusion that the two gels are well-tolerated by the patients.

On the basis of these observations, it may be concluded that patients suffering from common acne can be treated with 0.3% adapalene gel, such an exposure to adapalene being described as weak or very weak under clinical conditions.

It therefore ensues from these various studies that a pharmaceutical composition containing 0.3% of adapalene exhibits a benefit/risk ratio which makes it particularly suitable for the treatment of dermatological maladies having an inflammatory or proliferative component, and in particular, common acne.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for treating common acne, comedones, polymorphous acne, nodulocystic acne, acne conglobata or secondary acne afflicting the skin of an individual in need of such treatment, comprising topically administering to said individual an effective amount of a pharmaceutical composition which consists essentially of: (a) 0.3% by weight of 6-[3-(1-adamantyl)-4-methoxyphenyl]-2-naphthanoic acid (adapalene) or salt thereof; (b) one or more ingredients selected from the group consisting of carbomer 940, carbomer 934, propylene glycol, perhydrosqualene, cyclomethicone, PEG-20 methyl glucose sesquistearate and methyl glucose sesquistearate; (c) water; and, (d) optionally, one or more additives selected from the group consisting of wetting agents, pH regulators, osmotic pressure modifiers, emulsifiers, UV-A and UV-B screening agents and antioxidants; said composition being a gel or a cream.

2. The method according to claim 1, wherein said individual is afflicted with common acne.

3. The method according to claim 2, wherein the common acne is of moderate to moderately severe intensity.

4. A method for treating common acne, comedones, polymorphous acne, nodulocystic acne, acne conglobata or secondary acne afflicting the skin of an individual in need of such treatment, comprising topically administering to said individual an effective amount of a pharmaceutical composition which is a gel consisting essentially of 0.3% by weight of adapalene, carbomer 940, disodium edetate, methyl paraben, poloxamer 124, propylene glycol, sodium hydroxide and purified water.

5. The method according to claim 4, wherein said individual is afflicted with common acne.

6. A regime or regimen for treating common acne, comedones, polymorphous acne, nodulocystic acne, acne conglobata or secondary acne afflicting the skin of an individual in need of treatment, comprising topically administering to such individual an effective amount of a pharmaceutical composition which consists essentially of: 0.3% by weight of 6-[3-(1-adamantyl)-4-methoxyphenyl]-2-naphthanoic acid (adapalene) or salt thereof; one or more ingredients selected from the group consisting of carbomer 940, carbomer 934, propylene glycol, perhydrosqualene, cyclomethicone, PEG-20 methyl glucose sesquistearate, methyl glucose sesquistearate, water, alcohol and polyethylene glycol; and optionally, one or more additives selected from the group consisting of wetting agents, flavor enhancers, preservatives, stabilizers, moisture regulators, pH regulators, osmotic pressure modifiers, emulsifiers, UV-A and UV-B screening agents and antioxidants.

7. The regime or regimen according to claim 6, wherein said individual is afflicted with common acne.

8. The regime or regimen according to claim 7, wherein the common acne is of moderate to moderately severe intensity.

9. The regime or regimen according to claim 6, wherein the composition is a gel.

10. The regime or regimen according to claim 8, wherein the composition is a gel.

11. The regime or regimen according to claim 8, wherein the composition is a gel.

12. A method for treating common acne, comedones, polymorphous acne, nodulocystic acne, acne conglobata or secondary acne afflicting the skin of an individual in need of such treatment, consisting essentially of topically administering to said individual an effective amount of a pharmaceutical composition which consists essentially of: (a) 0.3% by weight of 6-[3-(1-adamantyl)-4-methoxyphenyl]-2-naphthanoic acid (adapalene) or salt thereof; (b) one or more ingredients selected from the group consisting of carbomer 940, carbomer 934, propylene glycol, perhydrosqualene, cyclomethicone, PEG-20 methyl glucose sesquistearate and methyl glucose sesquistearate; (c) water; and, (d) optionally, one or more additives selected from the group consisting of wetting agents, pH regulators, osmotic pressure modifiers, emulsifiers, UV-A and UV-B screening agents and antioxidants; said composition being a gel or a cream.

13. The method according to claim 12, wherein said individual is afflicted with common acne.

14. The method according to claim 13, wherein the common acne is of moderate to moderately severe intensity.

15. The method according to claim 12, wherein the composition is a gel consisting essentially of adapalene, carbomer 940, disodium edetate, methyl paraben, poloxamer 124, propylene glycol, sodium hydroxide and purified water.

16. The method according to claim 15, wherein said individual is afflicted with common acne.

17. A regime or regimen for treating common acne, comedones, polymorphous acne, nodulocystic acne, acne conglobata or secondary acne afflicting the skin of an individual in need of treatment, consisting essentially of topically administering to such individual an effective amount of a pharmaceutical composition which consists essentially of: 0.3% by weight of 6-[3-(1-adamantyl)-4-methoxyphenyl]-2-naphthanoic acid (adapalene) or salt thereof; one or more ingredients selected from the group consisting of carbomer 940, carbomer 934, propylene glycol, perhydrosqualene, cyclomethicone, PEG-20 methyl glucose sesquistearate, methyl glucose sesquistearate, water, alcohol and polyethylene glycol; and optionally, one or more additives selected from the group consisting of wetting agents, flavor enhancers, preservatives, stabilizers, moisture regulators, pH regulators, osmotic pressure modifiers, emulsifiers, UV-A and UV-B screening agents and antioxidants.

18. The regime or regimen according to claim 17, wherein said individual is afflicted with common acne.

19. The regime or regimen according to claim 18, wherein the common acne is of moderate to moderately severe intensity.

20. The regime or regimen according to claim 17, wherein the composition is a gel.

21. The regime or regimen according to claim 18, wherein the composition is a gel.

22. The regime or regimen according to claim 19, wherein the composition is a gel.

23. A method for treating common acne, comedones, polymorphous acne, nodulocystic acne, acne conglobata or secondary acne afflicting the skin of an individual in need of such treatment, comprising topically administering to said individual an effective amount of a pharmaceutical composition which comprises 0.3% by weight of 6-[3-(1-adamantyl)-4-methoxyphenyl]-2-naphthanoic acid (adapalene) or salt thereof, as the sole active anti-acne agent, formulated into a pharmaceutically acceptable medium therefor, said composition being a gel or a cream.

24. The method according to claim 23, wherein said individual is afflicted with common acne.

25. The method according to claim 23, wherein the common acne is of moderate to moderately severe intensity.

26. The method according to claim 23, wherein the composition is a gel comprising adapalene, carbomer 940, disodium edetate, methyl paraben, poloxamer 124, propylene glycol, sodium hydroxide and purified water.

27. The method according to claim 24, wherein the composition is a gel comprising adapalene, carbomer 940, disodium edentate, methyl paraben, poloxamer 124, propylene glycol, sodium hydroxide and purified water.

28. A regime or regimen for treating common acne, comedones, polymorphous acne, nodulocystic acne, acne conglobata or secondary acne afflicting the skin of an individual in need of treatment, comprising topically administering to such individual an effective amount of a pharmaceutical composition which comprises 0.3% by weight of 6-[3-(1-adamantyl)-4-methoxyphenyl]-2-naphthanoic acid (adapalene) or salt thereof, as the sole active anti-acne agent, formulated into a pharmaceutically acceptable medium therefor.

29. The regime or regimen according to claim 28, wherein said individual is afflicted with common acne.

30. The regime or regimen according to claim 29, wherein the common acne is of moderate to moderately severe intensity.

31. The regime or regimen according to claim 28, wherein the composition is a gel.

32. The regime or regimen according to claim 29, wherein the composition is a gel.

33. The regime or regimen according to claim 30, wherein the composition is a gel.

34. A method for treating common acne, comedones, polymorphous acne, nodulocystic acne, acne conglobata or secondary acne afflicting the skin of an individual in need of such treatment, comprising topically administering to said individual an effective amount of a pharmaceutical composition which is a gel consisting of 0.3% by weight of adapalene, carbomer 940, disodium edetate, methyl paraben, poloxamer 124, propylene glycol, sodium hydroxide and purified water.

35. The method according to claim 34, wherein said individual is afflicted with common acne.

* * * * *